US008012926B2

(12) United States Patent
Abe et al.

(10) Patent No.: US 8,012,926 B2
(45) Date of Patent: *Sep. 6, 2011

(54) AMINO ACID COMPOSITION AND SUPPLEMENTARY LIQUID CONTAINING THE SAME

(75) Inventors: Takashi Abe, Warabi (JP); Yasuko Sawai, Tokyo (JP)

(73) Assignees: Riken, Wako-shi (JP); Meiji Dairies Corporation, Tokyo (JP); Takashi Abe, Warabi-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/345,003

(22) Filed: Dec. 29, 2008

(65) Prior Publication Data

US 2009/0117208 A1      May 7, 2009

Related U.S. Application Data

(63) Continuation of application No. 11/289,383, filed on Nov. 30, 2005, which is a continuation of application No. PCT/JP2004/007850, filed on May 31, 2004.

(30) Foreign Application Priority Data

May 30, 2003   (JP) ................................. 2003-155397

(51) Int. Cl.
    *A61K 38/00*   (2006.01)
(52) U.S. Cl. ....................................................... 514/1.1
(58) Field of Classification Search ................ 514/2, 1.1
    See application file for complete search history.

(56) References Cited

U.S. PATENT DOCUMENTS

| 5,276,018 | A | 1/1994 | Wilmore |
| 5,310,768 | A | 5/1994 | Vinnars |
| 5,719,119 | A | 2/1998 | Veech |
| 5,719,134 | A | 2/1998 | Schmidl et al. |
| 6,287,757 | B1 * | 9/2001 | Abe et al. ........................ 435/4 |
| 2002/0106436 | A1 | 8/2002 | Gohman et al. |

FOREIGN PATENT DOCUMENTS

| EP | 689835 | 1/1996 |
| EP | 0 983 726 | 3/2000 |
| JP | 3-500775 | 2/1991 |
| JP | 3-128318 | 5/1991 |
| JP | 4-95026 | 3/1992 |
| JP | 4-95065 | 3/1992 |
| JP | 4-112825 | 4/1992 |
| JP | 5-58889 | 3/1993 |
| JP | 5-186533 | 7/1993 |
| JP | 6-336426 | 12/1994 |
| JP | 6-336432 | 12/1994 |
| JP | 8-73351 | 3/1996 |
| JP | 8-502039 | 3/1996 |
| JP | 8-502939 | 3/1996 |
| JP | 2518692 | 5/1996 |
| JP | 9-52828 | 2/1997 |
| JP | 9-249556 | 9/1997 |
| JP | 9-294565 | 11/1997 |
| JP | 11-302163 | 11/1999 |
| JP | 11-302164 | 11/1999 |
| JP | 2000-72669 | 3/2000 |
| WO | WO89/03688 | 5/1989 |
| WO | WO 91/09524 | 7/1991 |

OTHER PUBLICATIONS

Abe et al. Jpn. J. Phys. Fitness Sports Med., (1995), vol. 44, No. 2, pp. 225-238.
Bazzarre et al, Journal of the American College of Nutrition, (1992), vol. 11, No. 5, pp. 501-511.
Abe et al. Comp. Biochem. Physiol., (1991), vol. 99C, No. 1/2, pp. 79-84.
Tian Ye, et al. "Dynamic Effect of Intermittent Exercise on LA, LDH and the Influence of Oral Glutamine", Partial English Translation and English Abstract, pp. 1-29, (1993).
Takashi Abe, "Effect of Vespa Amino Acid Mixture from Hornet Larval Saliva on Endurance Exercise", Honeybee Science, 16(1), 1995, pp. 1-8 (with English Abstract on p. 8).

* cited by examiner

*Primary Examiner* — Kevin E Weddington
(74) *Attorney, Agent, or Firm* — Oblon, Spivak, McClelland, Maier & Neustadt, L.L.P.

(57) ABSTRACT

An amino acid composition comprises alanine, arginine, aspartic acid, glutamic acid, glycine, histidine, isoleucine, leucine, lysine, methionine, phenylalanine, proline, serine, threonine, tryptophan, tyrosine, valine, and glutamine. The amino acid composition of the present invention has such an effect that it can improve the action of promoting the process wherein the body fat is converted into the energy required for the physical exercise during and/or after the anoxic motions performed under an extremely high load.

15 Claims, 4 Drawing Sheets

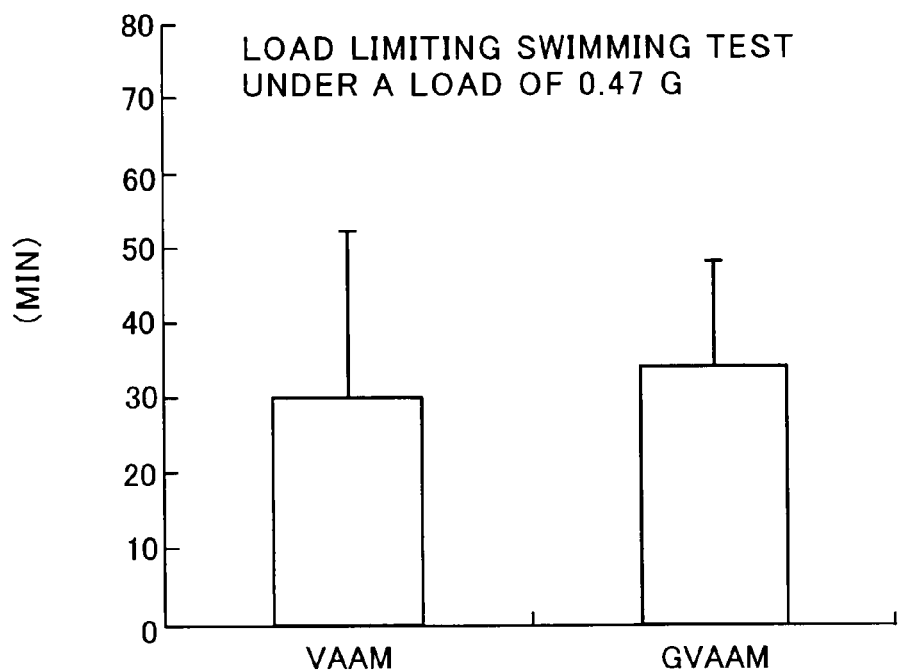
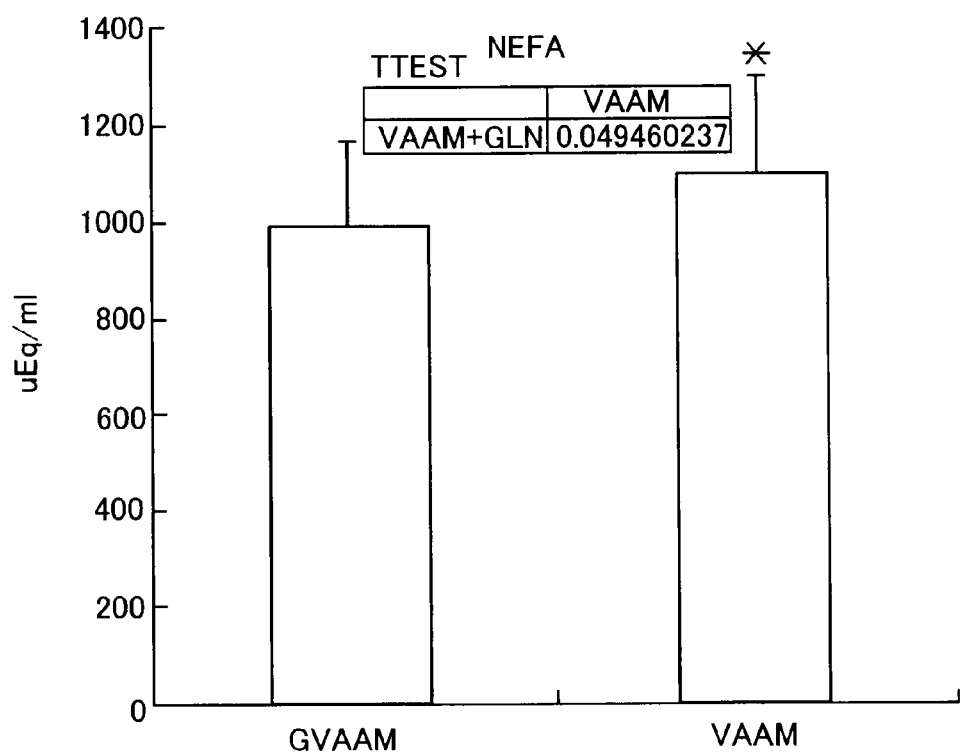

US 8,012,926 B2

AMINO ACID COMPOSITION AND SUPPLEMENTARY LIQUID CONTAINING THE SAME

This application is a continuation of U.S. application Ser. No. 11/289,383, filed Nov. 30, 2005, which is a continuation of PCT/JP04/007850, filed May 31, 2005, both of which are incorporated by reference in their entireties.

TECHNICAL FIELD

The present invention relates to an amino acid composition obtained on the basis of the knowledge concerning the composition composed of amino acids included in the saliva secreted by the larvae of wasps (belonging to the genus *Vespa*) and more specifically to an amino acid composition which permits the compensation of any reduction in the blood amino acid concentration associated with the hard or immoderate physical exercise and has effects of improving the human motor functions and effects of reducing fatigues and of recovering from the same after the physical exercise and which also has such an effect that it can improve the action of promoting the process wherein the body fat is converted into the energy required for the physical exercise during and/or after the anoxic motions performed under an extremely high load, as well as a supplementary liquid containing the same.

BACKGROUND ARTS

The inventors of this invention have conducted various studies of the saliva secreted by the larvae of various kinds of wasps belonging to the genus *Vespa* and have already proved that the nutritive liquid originated from the wasps can control the formation of substances involved in the fatigues, prevent the reduction of the blood sugar level and improve the capacity of locomotion, during exercise (see Patent Document 1 specified below). The inventors of this invention have further proved that the working mechanism of the same is to promote the conversion of body fat into the energy required for exercise (see Non-Patent Document 1 specified below). It has also been suggested that the VAAM (Vespa Amino Acid Mixture) as the principal component of the nutritive liquid has a variety of effects such as the recovery from the fatigues accompanied by the physical exercise, in addition to the foregoing effects (see, Patent Document Nos. 2 to 5 specified below).

On the other hand, it has been well known that the physical exhaustion due to the physical exercise would result in the significant destruction or loss of the amino acid balance in the blood (see Non-Patent Document 2 specified below). It has been believed that this would be caused as a result of the weariness and destruction of the body tissues due to the stresses associated with the physical exercise. However, there has not yet been focused on the physiological meanings and significance thereof until now.

The inventors of this invention have further investigated the blood amino acid concentration observed after the practice of exercise and the amino acid composition of VAAM and have thus found that the amino acid composition of VAAM has an extremely high correlation with the blood amino acids whose concentrations are reduced in proportion to the fatigues due to the practice of exercise. In other words, it has been proved that the amino acids, which are reduced in considerably high rates due to the fatigue, are included in VAAM in proportional higher amounts. Accordingly, it would be recognized that the supplementation of these amino acids is indispensable to the improvement of the motor functions and the recovery from the fatigues (see Patent Document 6 specified below). On the other hand, it has likewise been proved that trehalose can markedly increase the concentration of non-esterified fatty acid (NEFA) in the mouse serum during the movement thereof (see Patent Document 7 specified below). In this respect, the nutritive liquid of the wasps contains trehalose in a substantial amount (see Non-Patent Document 3 specified below). Thus, it has been found that the simultaneous administration of trehalose and VAAM permits the more intensive improvement of the motor functions (see Patent Document 8 specified below).

As has been discussed above, VAAM may serve to promote the process for converting the body fat into the energy required for the movement or exercise under the aerobic continuous motion. This function of VAAM would be quite effective for the motions over a long period of time such as a marathon race, but it is not always effective for the strong motional loads within a quite short period of time. For this reason, there has been a need for the development of an amino acid mixture which would be more effective for such high-load motions within a quite short period of time.

Patent Document 1: Japanese Patent No. 2,518,692;
Patent Document 2: Japanese Un-Examined Patent Publication (hereunder referred to as "JP-A") Hei 4-95026;
Patent Document 3: JP-A-Hei 4-112825;
Patent Document 4: JP-A-Hei 6-336426
Patent Document 5: JP-A-Hei 6-336432
Patent Document 6: JP-A-Hei 9-249556 (US-BA-6224861; EP-B1-873754);
Patent Document 7: JP-A-Hei 5-186353
Patent Document 8: JP-A-2000-72669 (US-BA-6287757; EP-A1-983726);
Non-Patent Document 1: ABE et al., Jap. J. Physical Fitness & Sports Med., 1995, 44:225;
Non-Patent Document 2: T. Bazzarre et al., J. Am. Collage Nutr., 1992, 11:501-511;
Non-Patent Document 3: ABE et al., Comp. Biochem. Physiol., 1991, 99C:79.

DISCLOSURE OF THE INVENTION

Accordingly, it is an object of the present invention to provide an amino acid composition having such an effect that it can improve the action of promoting the process wherein the body fat is converted into the energy required for the physical exercise during and/or after the anoxic or anaerobic motions performed under an extremely high load.

It is another object of the present invention to provide an amino acid composition which can inhibit the increase in the lactic acid level due to the anoxic physical exercise as low as possible, while maintaining the ability of VAAM to improve the motor functions at the highest possible level.

It is a further object of the present invention to provide a supplementary liquid containing the foregoing amino acid composition.

Thus, the present invention herein provides an amino acid composition and a supplementary liquid containing the same, such as those detailed below:

1. An amino acid composition comprising alanine, arginine, aspartic acid, glutamic acid, glycine, histidine, isoleucine, leucine, lysine, methionine, phenylalanine, proline, serine, threonine, tryptophan, tyrosine, valine, and glutamine.

2. An amino acid composition comprising the following amino acids in the molar ratios specified below: alanine (not more than 12 moles), arginine (not more than 5 moles), aspartic acid (not more than one mole), glutamic acid (not more than 4 moles), glycine (7 to 20 moles), histidine (not more than 5 moles), isoleucine (3 to 9 moles), leucine (2 to 12 moles), lysine (5 to 11 moles), methionine (not more than 5 moles), phenylalanine (0.5 to 5 moles), proline (4 to 30 moles), serine (not more than 5 moles), threonine (2 to 15 moles), tryptophan (not more than 5 moles), tyrosine (1 to 9 moles), valine (4 to 8 moles), and glutamine (0.01 to 20 moles).

3. An amino acid composition comprising alanine, arginine, aspartic acid, glycine, histidine, isoleucine, leucine, lysine, methionine, phenylalanine, proline, serine, threonine, tryptophan, tyrosine, valine, and glutamine.

4. An amino acid composition comprising the following amino acids in the molar ratios specified below: alanine (not more than 12 moles), arginine (not more than 5 moles), aspartic acid (not more than one mole), glycine (7 to 20 moles), histidine (not more than 5 moles), isoleucine (3 to 9 moles), leucine (2 to 12 moles), lysine (5 to 11 moles), methionine (not more than 5 moles), phenylalanine (0.5 to 5 moles), proline (4 to 30 moles), serine (not more than 5 moles), threonine (2 to 15 moles), tryptophan (not more than 5 moles), tyrosine (1 to 9 moles), valine (4 to 8 moles), and glutamine (0.01 to 20 moles).

5. An amino acid composition comprising alanine, arginine, aspartic acid, glutamic acid, glycine, histidine, isoleucine, leucine, lysine, methionine, phenylalanine, proline, serine, threonine, tyrosine, valine, and glutamine.

6. An amino acid composition comprising the following amino acids in the molar ratios specified below: alanine (not more than 12 moles), arginine (not more than 5 moles), aspartic acid (not more than one mole), glutamic acid (not more than 4 moles), glycine (7 to 20 moles), histidine (not more than 5 moles), isoleucine (3 to 9 moles), leucine (2 to 12 moles), lysine (5 to 11 moles), methionine (not more than 5 moles), phenylalanine (0.5 to 5 moles), proline (4 to 30 moles), serine (not more than 5 moles), threonine (2 to 15 moles), tyrosine (1 to 9 moles), valine (4 to 8 moles), and glutamine (0.01 to 20 moles).

7. An amino acid composition comprising alanine, arginine, glutamic acid, glycine, histidine, isoleucine, leucine, lysine, phenylalanine, proline, serine, threonine, tryptophan, tyrosine, valine, and glutamine.

8. An amino acid composition comprising the following amino acids in the molar ratios specified below: alanine (not more than 12 moles), arginine (not more than 5 moles), glutamic acid (not more than 4 moles), glycine (7 to 20 moles), histidine (not more than 5 moles), isoleucine (3 to 9 moles), leucine (2 to 12 moles), lysine (5 to 11 moles), phenylalanine (0.5 to 5 moles), proline (4 to 30 moles), serine (not more than 5 moles), threonine (2 to 15 moles), tryptophan (not more than 5 moles), tyrosine (1 to 9 moles), valine (4 to 8 moles), and glutamine (0.01 to 20 moles).

9. An amino acid composition comprising alanine, arginine, aspartic acid, glutamic acid, glycine, histidine, isoleucine, leucine, lysine, methionine, phenylalanine, proline, serine, threonine, tryptophan, tyrosine, valine, and glutamine.

10. An amino acid composition comprising the following amino acids in the molar ratios specified below: alanine (8.4 to 15.6 moles), arginine (2.4 to 4.6 moles), aspartic acid (not more than one mole), glutamic acid (2.2 to 10.4 moles), glycine (13.3 to 24.9 moles), histidine (1.8 to 11.9 moles), isoleucine (3.1 to 5.9 moles), leucine (4.3 to 8.1 moles), lysine (6.0 to 11.2 moles), methionine (not more than one mole), phenylalanine (2.6 to 5.0 moles), proline (12.6 to 23.4 moles), serine (1.7 to 3.3 moles), threonine (5.0 to 9.4 moles), tryptophan (1.5 to 2.9 moles), tyrosine (4.2 to 7.8 moles), valine (8.2 to 15.4 moles), and glutamine (0.01 to 20 moles).

11. An amino acid composition comprising alanine, arginine, aspartic acid, glycine, histidine, isoleucine, leucine, lysine, methionine, phenylalanine, proline, serine, threonine, tryptophan, tyrosine, valine, and glutamine.

12. An amino acid composition comprising the following amino acids in the molar ratios specified below: alanine (8.4 to 15.6 moles), arginine (2.4 to 4.6 moles), aspartic acid (not more than one mole), glycine (13.3 to 24.9 moles), histidine (1.8 to 11.9 moles), isoleucine (3.1 to 5.9 moles), leucine (4.3 to 8.1 moles), lysine (6.0 to 11.2 moles), methionine (not more than one mole), phenylalanine (2.6 to 5.0 moles), proline (12.6 to 23.4 moles), serine (1.7 to 3.3 moles), threonine (5.0 to 9.4 moles), tryptophan (1.5 to 2.9 moles), tyrosine (4.2 to 7.8 moles), valine (8.2 to 15.4 moles), and glutamine (0.01 to 20 moles).

13. An amino acid composition comprising alanine, arginine, aspartic acid, glutamic acid, glycine, histidine, isoleucine, leucine, lysine, methionine, phenylalanine, proline, serine, threonine, tyrosine, valine, and glutamine.

14. An amino acid composition comprising the following amino acids in the molar ratios specified below: alanine (8.4 to 15.6 moles), arginine (2.4 to 4.6 moles), aspartic acid (not more than one mole), glutamic acid (2.2 to 10.4 moles), glycine (13.3 to 24.9 moles), histidine (1.8 to 11.9 moles), isoleucine (3.1 to 5.9 moles), leucine (4.3 to 8.1 moles), lysine (6.0 to 11.2 moles), methionine (not more than one mole), phenylalanine (2.6 to 5.0 moles), proline (12.6 to 23.4 moles), serine (1.7 to 3.3 moles), threonine (5.0 to 9.4 moles), tyrosine (4.2 to 7.8 moles), valine (8.2 to 15.4 moles), and glutamine (0.01 to 20 moles).

15. An amino acid composition comprising alanine, arginine, glutamic acid, glycine, histidine, isoleucine, leucine, lysine, phenylalanine, proline, serine, threonine, tryptophan, tyrosine, valine, and glutamine.

16. An amino acid composition comprising the following amino acids in the molar ratios specified below: alanine (8.4 to 15.6 moles), arginine (2.4 to 4.6 moles), glutamic acid (2.2 to 10.4 moles), glycine (13.3 to 24.9 moles), histidine (1.8 to 11.9 moles), isoleucine (3.1 to 5.9 moles), leucine (4.3 to 8.1 moles), lysine (6.0 to 11.2 moles), phenylalanine (2.6 to 5.0 moles), proline (12.6 to 23.4 moles), serine (1.7 to 3.3 moles), threonine (5.0 to 9.4 moles), tryptophan (1.5 to 2.9 moles), tyrosine (4.2 to 7.8 moles), valine (8.2 to 15.4 moles), and glutamine (0.01 to 20 moles).

17. A supplementary liquid comprising the amino acid composition as set forth in any one of the foregoing items 1 to 16.

BRIEF DESCRIPTION OF THE DRAWINGS

FIG. 3 is a diagram showing the results observed when GVAAM or VAAM was orally administered to mice, followed by allowing these mice to swim under a load of 0.47 g.

FIG. 4 is a diagram showing the free fatty acid values (NEFA values) observed after GVAAM or VAAM was orally administered to mice and these mice were then allowed to swim under a load of 0.47 g. In this figure, the asterisk (*) indicates that there is observed a significant difference ($p<0.05$).

BEST MODE FOR CARRYING OUT THE INVENTION

Figure 1:
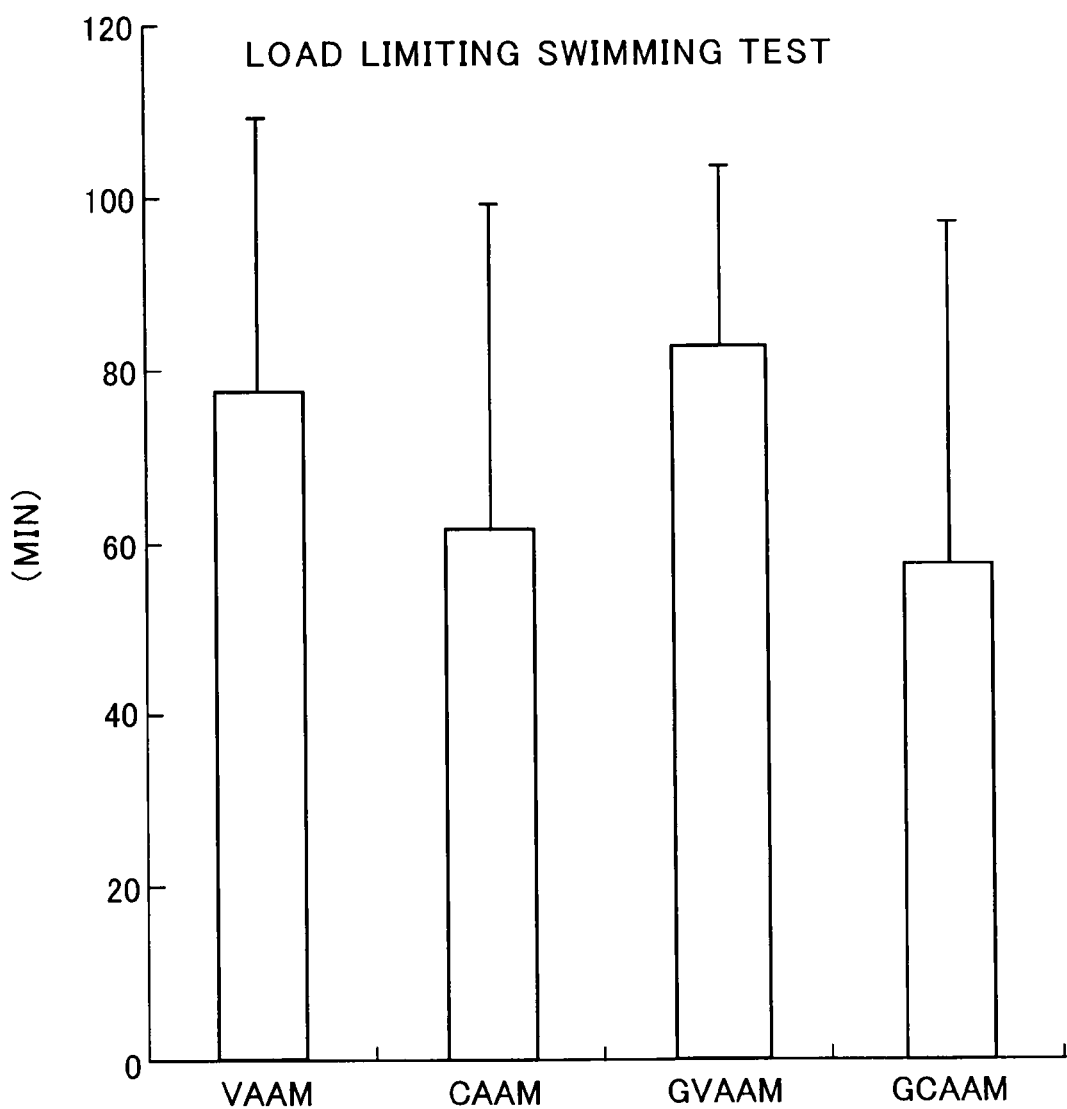
FIG. 1 is a diagram showing the results observed when GVAAM, GCAAM, VAAM or CAAM was orally administered to mice, followed by allowing these mice to swim under a load of 0.3 g.

It has been proved that the VAAM can serve to collectively activate various kinds of physical functions required during exercise or motions. The VAAM is insufficient in such a function to improve the ability of taking anoxic exercise or motions under a high load. For this reason, the composition of the VAAM as an amino acid mixture has been variously designed so that a rise of the lactic acid level originated from the anoxic motions should be controlled to a lowest possible level, while maintaining the function of improving the motor functions as much as possible. The inventors have conducted repeated trial and error using mice and a motor load stronger than that conventionally used (for instance, allowing the mice to swim or to instantaneously move) to thus obtain an amino acid composition which can cope with the anoxic motions as much as possible. As a result, the inventors have found that an amino acid composition effective even for the anoxic motions, during which a stronger load is applied, can be obtained if glutamine is incorporated into the conventional VAAM which can cope with the aerobic continuous motions and have thus completed the present invention. The present invention will now be described in more detail below.

The basic amino acid composition used in the present invention is one disclosed in, for instance, the foregoing Patent Document Nos. 1 to 8 and Non-Patent Document Nos. 1 to 3 and particularly preferably used herein is VAAM. The amount of glutamine to be added to the basic amino acid composition ranges from 0.01 to 20 moles, preferably 1.0 to 15 moles and more preferably 2.0 to 10 moles per 100 moles of the amino acid composition. If the added amount of glutamine is less than 0.01 mole, the intended effect expected by the addition thereof is insufficient, while if it exceeds 20 moles, a problem arises, such that the blood lactic acid level is increased.

Trehalose may be incorporated into the amino acid composition of the present invention as disclosed in Patent Document 8. The amount of trehalose to be incorporated into the amino acid composition of the invention preferably ranges from (0.45 to 1.6): (0.5 to 5.0) and more preferably (0.8 to 1.6): (1.0 to 4.0) as expressed in terms of the mass ratio of the amino acid composition to trehalose.

The amino acid composition of the present invention may comprise, in addition to the foregoing amino acids, taurine (Tau) (preferably not more than 3% by mole), phosphoric acid ethanolamine (P-EtAm) (preferably not more than 2% by mole), cystine (Cys) (preferably not more than 0.5% by mole), β-alanine (β-Ala) (preferably not more than 1% by mole), γ-aminobutyric acid (GABA) (preferably not more than 0.5% by mole), ornithine (Orn) or ethanolamine (EtAm) (preferably not more than 3% by mole), ammonia ($NH_3$) (preferably not more than 2% by mole), 1-methyl-histidine (1-MeHis) (preferably not more than 3% by mole), 3-methyl-histidine (3-MeHis) (preferably not more than 1% by mole). Preferably, the amino acids present in the amino acid composition used in the invention are, in particular, L-amino acids.

When preparing the amino acid composition of the present invention, it is sufficient that each of the aforementioned commercially available amino acids is admixed with the basic amino acid composition in each desired rate specified above.

In addition, when the amino acid composition is used as a supplementary liquid, the latter may be prepared by dissolving the former in distilled water. In this connection, it would be sufficient that the supplementary liquid is usually stored in the form of uniformly admixed composition and the composition is dissolved in distilled water in case of need. The temperature at which the composition of the present invention is prepared and stored is not restricted to any specific one, but it is preferred to prepare and store the composition, at a temperature of not more than room temperature. The composition of the present invention quite slightly tastes bitter, does not show a toxicity even when it is orally administered to mice in a dose of 20 g/kg and the $LD_{50}$ value thereof is thus extremely higher than 20 g/kg.

The composition of the present invention is useful as a medicine or a food such as a beverage. When using the same as a medicine, the routes of administration of the composition (medicine) is not restricted to any particular one and it may be administered through the currently used routes of administration such as oral and per rectal administration, as well as administration by injection and transfusion. In case of the oral administration, the composition having the foregoing composition may be used in the form of the composition as such or in the form of a variety of pharmaceutical preparations such as a tablet, a capsule, a powder, a troche or a syrup together with a pharmaceutically acceptable carrier or an excipient. In this case, however, it would sometimes require a long period of time for the absorption of the solid preparations such as tablets and powders and therefore, it is preferably administered through the oral route in the form of, for instance, a liquid preparation. In this case, the composition is preferably administered in the form of an aqueous solution prepared using appropriate additives, for instance, a salt such as sodium chloride, a buffering agent and/or a chelating agent. Moreover, when using the composition in the form of an injection, the latter is prepared by, for instance, dissolving the composition in sterilized distilled water together with appropriate additives such as a buffering agent and/or an isotonicity and the resulting injection is, for instance, intravenously administered through the intravenous drip injection. When the composition is used as a food, it may be formed into a drink by the addition of an appropriate flavoring agent, such as a refreshing beverage or a powdered beverage, for instance, a capsule or a tablet produced using the powdered composition obtained by the spray drying, freeze-drying or microfine powder-preparation technique.

The composition of the present invention has an extremely low toxicity and therefore, it can be administered in a quite wide dose range. The dose thereof may vary depending on the route of administration selected, each particular purpose of the use thereof, but in general ranges from 1 to 12 g/dose, 3 to 18 g/day and preferably 2 to 4 g/dose, 6 to 12 g/day, as expressed in terms of the solid content of the composition. When using the composition of the present invention as a supplementary liquid to be administered before the initiation of the exercise and during and after the exercise, the composition is used in the form of an aqueous solution having a concentration ranging from 0.8 to 3.8% by mass and the solution is suitably administered in an amount ranging from 200 to 500 ml over one to three times a day. When using the same as an injection, it is used in the form of an aqueous solution having a concentration ranging from 0.8 to 3.8% by mass and the solution is suitably administered through injection in an amount ranging from 100 to 400 ml/dose and preferably 150 to 300 ml/dose.

EXAMPLES

The present invention will hereunder be described in more specifically with reference to the following Test Examples and Examples, but the present invention is not restricted to these specific Examples at all.

Animals: To ddY♂ (6.8-week-old) mice which had been fasted for 12 to 16 hours, there were orally administered a variety of amino acid-containing liquid nutrients in an amount of 37.5 μl/g (body weight), they were then allowed to stand for 30 minutes and they were subsequently forced to swim in a water-flowing pool maintained at 35° C. In case of the swimming under the application of a load, a weight of 0.3 g or 0.47 g was attached to the tail of each mouse. The blood was collected from each mouse immediately after the animal was forced to swim for 30 minutes and it was then analyzed for the metabolites in blood.

Liquid Nutrients There were used GVAAM having the following amino acid composition and VAAM, CAAM (Casein amino acid mixture) and GCAAM as positive controls.

TABLE 1

| Amino acid | VAAM | CAAM | GVAAM | GCAAM |
|---|---|---|---|---|
| Asp | 0.17 | 6.55 | 0.17 | 6.55 |
| Thr | 7.03 | 4.28 | 7.03 | 4.28 |
| Ser | 2.14 | 5.54 | 2.14 | 5.54 |
| Glu | 3.86 | 20.26 | 3.86 | 20.26 |
| Pro | 17.03 | 10.63 | 17.03 | 10.63 |
| Gly | 11.76 | 1.81 | 11.76 | 1.81 |
| Ala | 4.47 | 2.82 | 4.47 | 2.82 |
| Val | 5.63 | 6.19 | 5.63 | 6.19 |
| Cys |  | 0.33 |  | 0.33 |
| Met | 0.7 | 2.56 | 0.7 | 2.56 |
| Ile | 4.87 | 4.97 | 4.87 | 4.97 |
| Leu | 6.61 | 8.75 | 6.61 | 8.75 |
| Tyr | 8.86 | 5.34 | 8.86 | 5.34 |
| Phe | 5.19 | 4.81 | 5.19 | 4.81 |
| Lys | 10.34 | 7.46 | 10.34 | 7.46 |
| Trp | 3.68 | 1.48 | 3.68 | 1.48 |
| His | 3.27 | 2.68 | 3.27 | 2.68 |
| Arg | 5.02 | 3.44 | 5.02 | 3.44 |
| Gln |  |  | 5.3 | 5.3 |

Biochemical Analysis of Blood

1. Blood Lactic Acid Level:

The blood lactic acid level as the indication of the fatigue-related substances observed when talking exercise was determined by collecting the blood of each test animal, removing the proteins present therein using 6% PCA to thus give the supernatant of the blood and then inspecting the NADH formed for the absorbance at 280 nm according to the Lactate Dehydrogenase technique described below in detail.

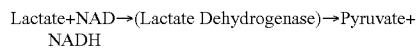
Lactate+NAD→(Lactate Dehydrogenase)→Pyruvate+ NADH

2. Blood Sugar Level:

The blood sugar level of each test animal was determined using the supernatant obtained after the PCA treatment like the determination of the blood lactic acid level, according to the Hexokinase technique specified below:

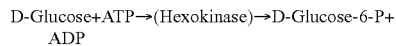
D-Glucose+ATP→(Hexokinase)→D-Glucose-6-P+ ADP

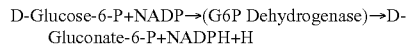
D-Glucose-6-P+NADP→(G6P Dehydrogenase)→D-Gluconate-6-P+NADPH+H

The amount of NADPH formed was determined according to OD (280 nm).

3. Free Fatty Acid Value:

The blood of each test animal was collected, followed by allowing it to stand for 30 minutes, subjecting the blood to centrifugation at 3000 rpm to thus obtain a supernatant (serum), which was used for the determination of the free fatty acid value. The determination was carried out using the following enzymatic technique:

Reaction Scheme:

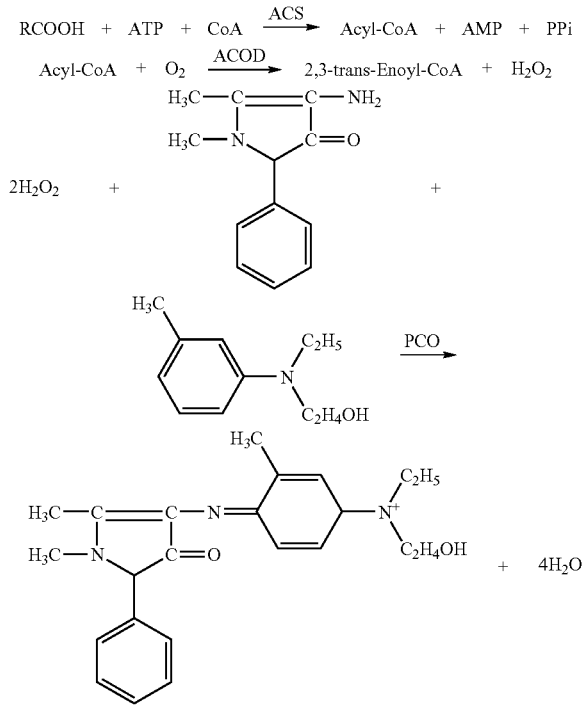

Results:

1. Effect of Improving Capacity for Locomotions as a Function of Increase of Applied Load Observed when Forcing Animals to Swim Under Applied Load There has conventionally been known that VAAM may serve to improve the overall ability of performing continuous motions under the aerobic respiratory conditions. Thus, mice were forced to undergo motions under the anaerobic respiratory conditions. To this end, weights were attached to the tails of mice when forcing the mice to swim while variously changing the weights to increase the rate of anaerobic motions. There were orally administered, to these mice, 4 kinds of amino acid-containing liquid nutrients, VAAM+glutamine (GVAAM), CAAM+glutamine (GCAAM), VAAM, and CAAM, while applying a load of 0.3 g to each test animal, and then these animals were forced to swim under the application of a load. As a result, it was found that the animals belonging to the GVAAM-administered group could swim for the longest time period and the swimming times were reduced in the order of the VAAM-administered group, the GCAAM-administered group and the CAAM-administered group (see FIG. 1).

Figure 2:
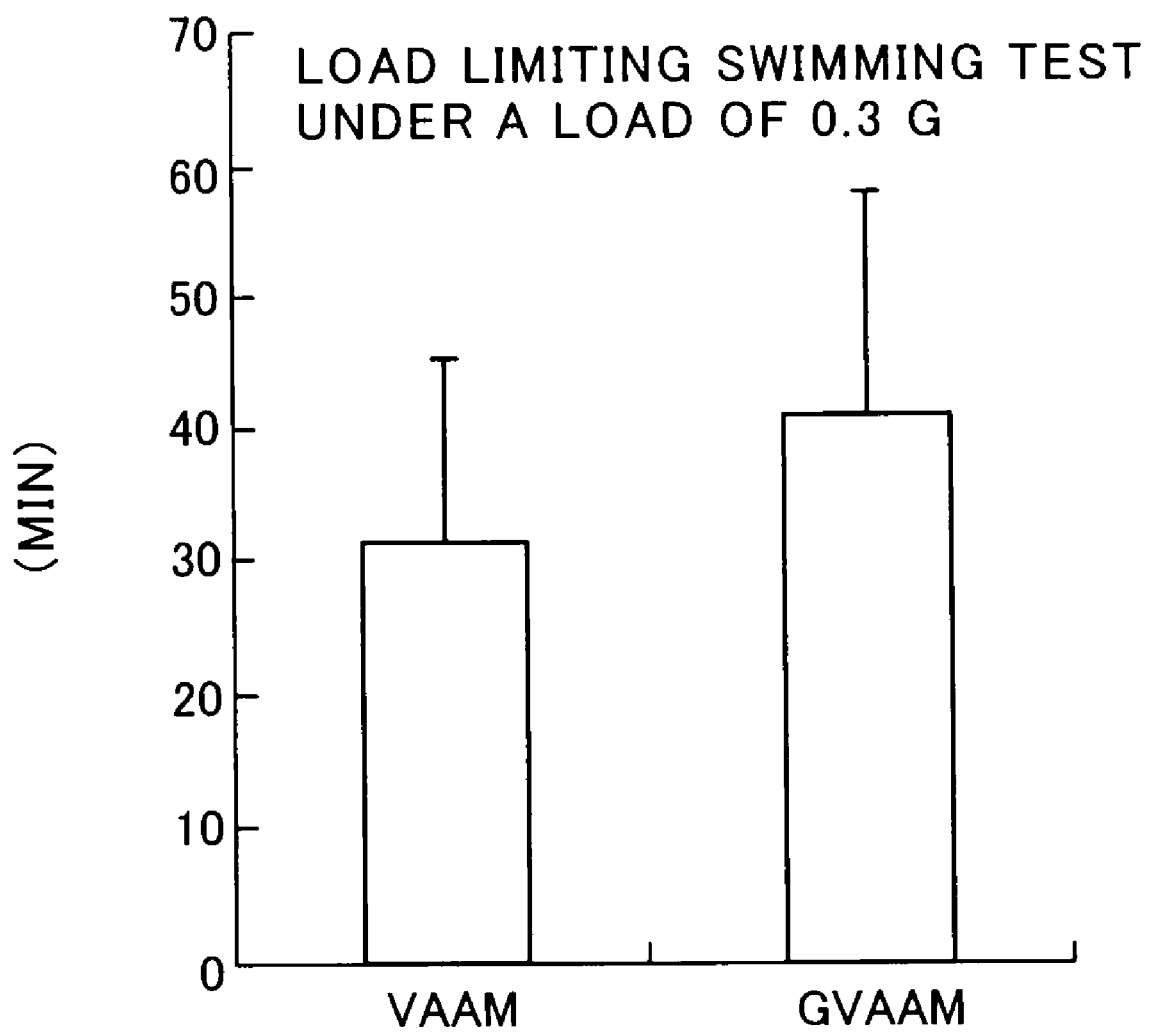
FIG. 2 is a diagram showing the results observed when GVAAM or VAAM was orally administered to mice, followed by allowing these mice to swim under a load of 0.3 g.

Then the effect was further investigated by comparing the effect observed for the GVAAM-administered group with that observed for the VAAM-administered group. The animals belonging to these groups (including 10 animals each) were again forced to swim while applying a load of 0.3 g and as a result, it was found that the animals of the GVAAM-administered group could swim for a longer time period at a significant difference (see FIG. 2).

The load applied to the animals during swimming was increased to 0.47 g in order to increase the rate of the anaerobic respiration and the results were compared with one another. As a result, it was found that the animals of the GVAAM-administered group could significantly swim over a longer time period like the foregoing swimming test performed under a lighter load (see FIG. 3).

The foregoing results clearly indicate that the amino acid composition GVAAM can promote or improve the capacity for locomotions as compared with VAAM, the extent of which increases as the load applied increases and the rate of the anaerobic respiratory motions becomes high.

2. Variations in Fatigue-Related Substances in Blood, Blood Sugar, Free Fatty Acid Level in Blood Up to now, it has been elucidated that VAAM can promote the combustion of fats during the aerobic continuous exercise, inhibit the increase in the amount or the accumulation of fatigue-related substances and further inhibit the reduction of the blood sugar level. In other words, VAAM can promote the conversion of fats into the energy required for motions or exercise and thus it can promote the ability to undergo aerobic continuous motions such as a long-distance running. Thus, a variety of hematic biochemical factors closely related to the motor functions of organisms were determined using the swimming motions under a high load of 0.47 g and those observed for the animals belonging to the GVAAM-administered group were compared with those observed for the animals belonging to the VAAM-administered group. As a result, the free fatty acid level (NEFA value) observed for the GVAAM-administered group was found to be significantly lower than that observed for the VAAM-administered group (see FIG. 4) and VAAM is superior to GVAAM in the fat-burning ability under the high load conditions. This clearly suggests that GVAAM generates the energy required for exercise, under the high load motions, according to a different mechanism, unlike VAAM which generates the energy required for motions through the acceleration of the combustion of fats.

Figure 5:
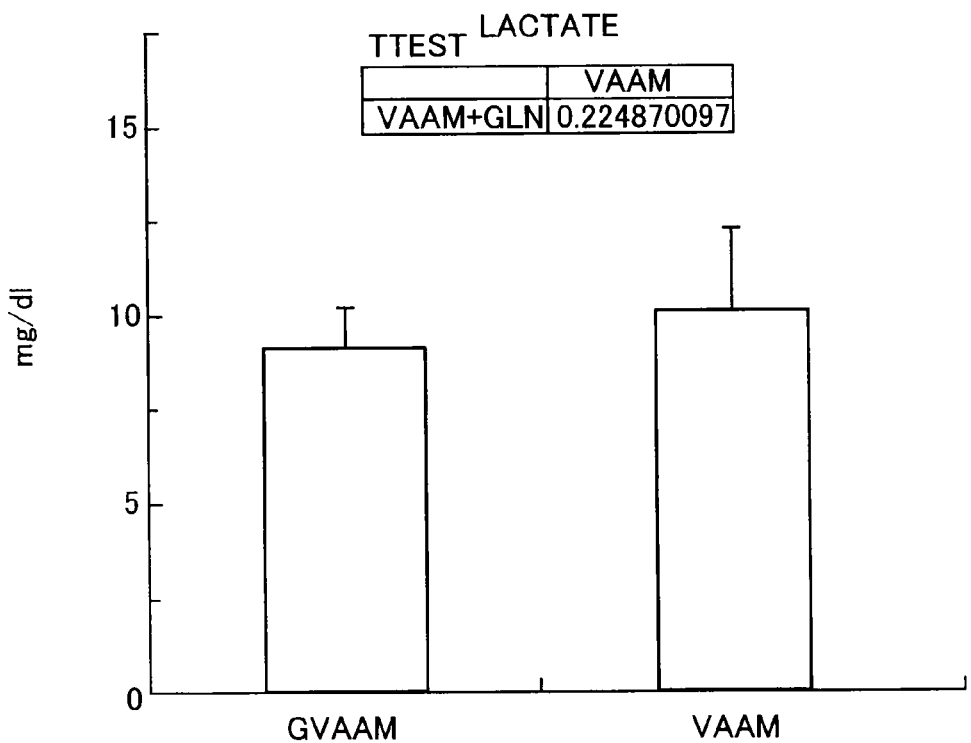
FIG. 5 is a diagram showing the blood lactic acid level observed after GVAAM or VAAM was orally administered to mice and these mice were then allowed to swim under a load of 0.47 g.
Figure 6:
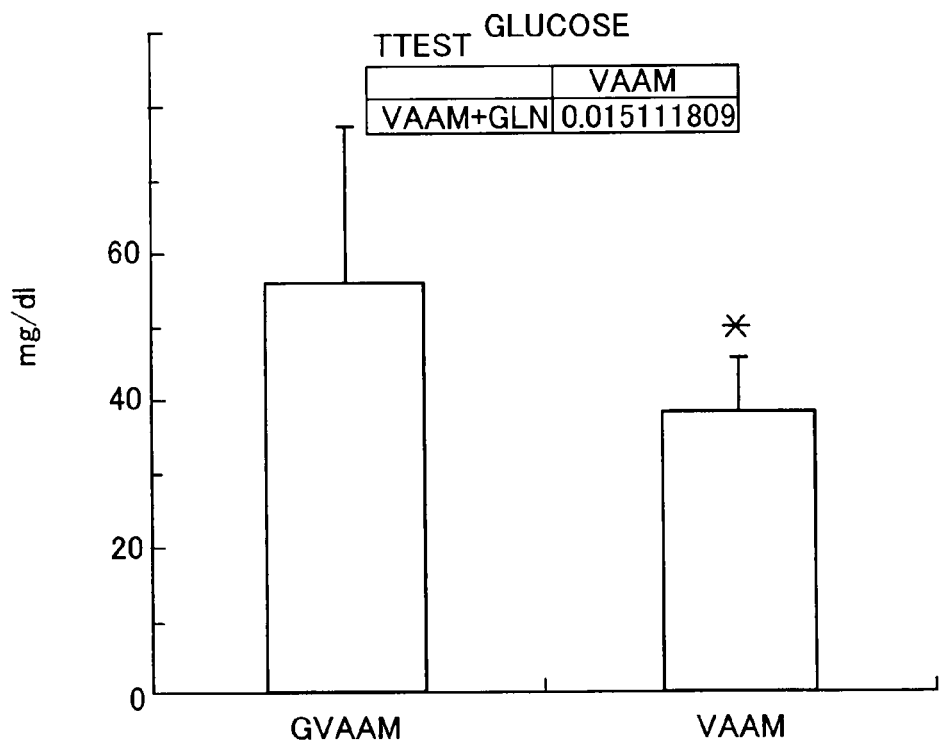
FIG. 6 is a diagram showing the blood sugar level observed after GVAAM or VAAM was orally administered to mice and these mice were then allowed to swim under a load of 0.47 g. In this figure, the asterisk (*) indicates that there is observed a significant difference (p<0.05).

The GVAAM-administered group is lower in the blood lactic acid level than the VAAM-administered group (see FIG. 5) and the former is significantly higher in the blood sugar value than the latter (see FIG. 6).

These results clearly indicate that, when taking exercise under a high-load in oxygen deficient or anaerobic conditions, GVAAM can promote the reduction of the lactic acid level and simultaneously promote the rise in the blood sugar level and thus leads to the improvement of the motor functions of organisms. This clearly suggests that GVAAM improves the motor functions according to the mechanism fundamentally different from that of the conventional VAAM which can improve the performance while making use of the energy originated from fats observed during the aerobic continuous motions.

INDUSTRIAL APPLICABILITY

The amino acid composition of the present invention is one obtained by the addition of glutamic acid as a glycogenic amino acid to another amino acid composition having a strong effect of accelerating motor functions such as VAAM, shows an effect of improving the motor functions during the anaerobic high-load motions, which is more effective than that achieved by VAAM and thus shows a strong effect of promoting or improving the motor functions under the anaerobic respiratory conditions.

What is claimed is:

1. A method for treating a subject undergoing anoxic and/or anaerobic exercise comprising administering to a subject in need thereof at least one of the following amino acid compositions:
   (a) an amino acid composition comprising the following amino acids in the molar ratios specified below: alanine (not more than 12 moles), arginine (not more than 5 moles), aspartic acid (not more than one mole), glutamic acid (not more than 4 moles), glycine (7 to 20 moles), histidine (not more than 5 moles), isoleucine (3 to 9 moles), leucine (2 to 12 moles), lysine (5 to 11 moles), methionine (not more than 5 moles), phenylalanine (0.5 to 5 moles), proline (4 to 30 moles), serine (not more than 5 moles), threonine (2 to 15 moles), tryptophan (not more than 5 moles), tyrosine (1 to 9 moles), valine (4 to 8 moles), and glutamine (0.01 to 20 moles);
   (b) an amino acid composition comprising the following amino acids in the molar ratios specified below: alanine (not more than 12 moles), arginine (not more than 5 moles), aspartic acid (not more than one mole), glycine (7 to 20 moles), histidine (not more than 5 moles), isoleucine (3 to 9 moles), leucine (2 to 12 moles), lysine (5 to 11 moles), methionine (not more than 5 moles), phenylalanine (0.5 to 5 moles), proline (4 to 30 moles), serine (not more than 5 moles), threonine (2 to 15 moles), tryptophan (not more than 5 moles), tyrosine (1 to 9 moles), valine (4 to 8 moles), and glutamine (0.01 to 20 moles);
   (c) an amino acid composition comprising the following amino acids in the molar ratios specified below: alanine (not more than 12 moles), arginine (not more than 5 moles), aspartic acid (not more than one mole), glutamic acid (not more than 4 moles), glycine (7 to 20 moles), histidine (not more than 5 moles), isoleucine (3 to 9 moles), leucine (2 to 12 moles), lysine (5 to 11 moles), methionine (not more than 5 moles), phenylalanine (0.5 to 5 moles), proline (4 to 30 moles), serine (not more than 5 moles), threonine (2 to 15 moles), tyrosine (1 to 9 moles), valine (4 to 8 moles), and glutamine (0.01 to 20 moles); or
   (d) an amino acid composition comprising the following amino acids in the molar ratios specified below: alanine (not more than 12 moles), arginine (not more than 5 moles), glutamic acid (not more than 4 moles), glycine (7 to 20 moles), histidine (not more than 5 moles), isoleucine (3 to 9 moles), leucine (2 to 12 moles), lysine (5 to 11 moles), phenylalanine (0.5 to 5 moles), proline (4 to 30 moles), serine (not more than 5 moles), threonine (2 to 15 moles), tryptophan (not more than 5 moles), tyrosine (1 to 9 moles), valine (4 to 8 moles), and glutamine (0.01 to 20 moles).

2. The method of claim 1 comprising:
   administering (a) an amino acid composition comprising the following amino acids in the molar ratios specified below: alanine (not more than 12 moles), arginine (not more than 5 moles), aspartic acid (not more than one mole), glutamic acid (not more than 4 moles), glycine (7 to 20 moles), histidine (not more than 5 moles), isoleucine (3 to 9 moles), leucine (2 to 12 moles), lysine (5 to 11 moles), methionine (not more than 5 moles), phenylalanine (0.5 to 5 moles), proline (4 to 30 moles), serine (not more than 5 moles), threonine (2 to 15 moles), tryptophan (not more than 5 moles), tyrosine (1 to 9 moles), valine (4 to 8 moles), and glutamine (0.01 to 20 moles);

wherein said subject is in need of promoting conversion of body fats into energy required for physical exercise during and/or after anoxic or anaerobic motions performed under an extremely high load.

3. The method of claim 1 comprising:

administering (b) an amino acid composition comprising the following amino acids in the molar ratios specified below: alanine (not more than 12 moles), arginine (not more than 5 moles), aspartic acid (not more than one mole), glycine (7 to 20 moles), histidine (not more than 5 moles), isoleucine (3 to 9 moles), leucine (2 to 12 moles), lysine (5 to 11 moles), methionine (not more than 5 moles), phenylalanine (0.5 to 5 moles), proline (4 to 30 moles), serine (not more than 5 moles), threonine (2 to 15 moles), tryptophan (not more than 5 moles), tyrosine (1 to 9 moles), valine (4 to 8 moles), and glutamine (0.01 to 20 moles);

wherein said subject is in need of promoting conversion of body fats into energy required for physical exercise during and/or after anoxic or anaerobic motions performed under an extremely high load.

4. The method of claim 1 comprising:

administering (c) an amino acid composition comprising the following amino acids in the molar ratios specified below: alanine (not more than 12 moles), arginine (not more than 5 moles), aspartic acid (not more than one mole), glutamic acid (not more than 4 moles), glycine (7 to 20 moles), histidine (not more than 5 moles), isoleucine (3 to 9 moles), leucine (2 to 12 moles), lysine (5 to 11 moles), methionine (not more than 5 moles), phenylalanine (0.5 to 5 moles), proline (4 to 30 moles), serine (not more than 5 moles), threonine (2 to 15 moles), tyrosine (1 to 9 moles), valine (4 to 8 moles), and glutamine (0.01 to 20 moles);

wherein said subject is in need of converting body fats into energy required for physical exercise during and/or after anoxic or anaerobic motions performed under an extremely high load.

5. The method of claim 1 comprising:

administering (d) an amino acid composition comprising the following amino acids in the molar ratios specified below: alanine (not more than 12 moles), arginine (not more than 5 moles), glutamic acid (not more than 4 moles), glycine (7 to 20 moles), histidine (not more than 5 moles), isoleucine (3 to 9 moles), leucine (2 to 12 moles), lysine (5 to 11 moles), phenylalanine (0.5 to 5 moles), proline (4 to 30 moles), serine (not more than 5 moles), threonine (2 to 15 moles), tryptophan (not more than 5 moles), tyrosine (1 to 9 moles), valine (4 to 8 moles), and glutamine (0.01 to 20 moles);

wherein said subject is in need of converting body fats into energy required for physical exercise during and/or after anoxic or anaerobic motions performed under an extremely high load.

6. The method of claim 1, wherein an amount of said composition sufficient to reduce fatigue, increase blood sugar level, or decrease lactic acid level, compared to a control subject not receiving said composition, is administered.

7. The method of claim 1, wherein said composition further comprises at least one of trehalose, taurine (Tau), phosphoric acid ethanolamine (P-EtAm), cysteine (Cys), β-alanine, γ-aminobutyric acid (GABA), ornithine (Orn), ethanolamine (EtAm), ammonia (NH$_3$), 1-methyl-histidine (1-MeHis), or 3-methyl-histidine (3-MeHis).

8. A method for treating a subject undergoing anoxic and/or aneaerobic exercise comprising administering to a subject in need thereof at least one of the following amino acid compositions:

(e) an amino acid composition comprising the following amino acids in the molar ratios specified below: alanine (8.4 to 15.6 moles), arginine (2.4 to 4.6 moles), aspartic acid (not more than one mole), glutamic acid (2.2 to 10.4 moles), glycine (13.3 to 24.9 moles), histidine (1.8 to 11.9 moles), isoleucine (3.1 to 5.9 moles), leucine (4.3 to 8.1 moles), lysine (6.0 to 11.2 moles), methionine (not more than one mole), phenylalanine (2.6 to 5.0 moles), proline (12.6 to 23.4 moles), serine (1.7 to 3.3 moles), threonine (5.0 to 9.4 moles), tryptophan (1.5 to 2.9 moles), tyrosine (4.2 to 7.8 moles), valine (8.2 to 15.4 moles), and glutamine (0.01 to 20 moles);

(f) an amino acid composition comprising the following amino acids in the molar ratios specified below: alanine (8.4 to 15.6 moles), arginine (2.4 to 4.6 moles), aspartic acid (not more than one mole), glycine (13.3 to 24.9 moles), histidine (1.8 to 11.9 moles), isoleucine (3.1 to 5.9 moles), leucine (4.3 to 8.1 moles), lysine (6.0 to 11.2 moles), methionine (not more than one mole), phenylalanine (2.6 to 5.0 moles), proline (12.6 to 23.4 moles), serine (1.7 to 3.3 moles) threonine (5.0 to 9.4 moles), tryptophan (1.5 to 2.9 moles), tyrosine (4.2 to 7.8 moles), valine (8.2 to 15.4 moles), and glutamine (0.01 to 20 moles)

(g) an amino acid composition comprising the following amino acids in the molar ratios specified below: alanine (8.4 to 15.6 moles), arginine (2.4 to 4.6 moles), aspartic acid (not more than one mole), glutamic acid (2.2 to 10.4 moles), glycine (13.3 to 24.9 moles), histidine (1.8 to 11.9 moles), isoleucine (3.1 to 5.9 moles), leucine (4.3 to 8.1 moles), lysine (6.0 to 11.2 moles), methionine (not more than one mole), phenylalanine (2.6 to 5.0 moles), proline (12.6 to 23.4 moles), serine (1.7 to 3.3 moles), threonine (5.0 to 9.4 moles), tyrosine (4.2 to 7.8 moles), valine (8.2 to 15.4 moles), and glutamine (0.01 to 20 moles); or (h) an amino acid composition comprising the following amino acids in the molar ratios specified below: alanine (8.4 to 15.6 moles), arginine (2.4 to 4.6 moles), glutamic acid (2.2 to 10.4 moles), glycine (13.3 to 24.9 moles), histidine (1.8 to 11.9 moles), isoleucine (3.1 to 5.9 moles), leucine (4.3 to 8.1 moles), lysine (6.0 to 11.2 moles), phenylalanine (2.6 to 5.0 moles), proline (12.6 to 23.4 moles), serine (1.7 to 3.3 moles), threonine (5.0 to 9.4 moles), tryptophan (1.5 to 2.9 moles), tyrosine (4.2 to 7.8 moles), valine (8.2 to 15.4 moles), and glutamine (0.01 to 20 moles).

9. The method of claim 8 for promoting a process wherein body fats are converted into energy required for physical exercise during and/or after anoxic or anaerobic motions performed under an extremely high load, which comprises:

administering (e) an amino acid composition comprising the following amino acids in the molar ratios specified below: alanine (8.4 to 15.6 moles), arginine (2.4 to 4.6 moles), aspartic acid (not more than one mole), glutamic acid (2.2 to 10.4 moles), glycine (13.3 to 24.9 moles), histidine (1.8 to 11.9 moles), isoleucine (3.1 to 5.9 moles), leucine (4.3 to 8.1 moles), lysine (6.0 to 11.2 moles), methionine (not more than one mole), phenylalanine (2.6 to 5.0 moles), proline (12.6 to 23.4 moles), serine (1.7 to 3.3 moles), threonine (5.0 to 9.4 moles), tryptophan (1.5 to 2.9 moles), tyrosine (4.2 to 7.8 moles), valine (8.2 to 15.4 moles), and glutamine (0.01 to 20 moles).

10. The method of claim 8 for promoting a process wherein body fats are converted into energy required for physical exercise during and/or after anoxic or anaerobic motions performed under an extremely high load, which comprises the steps of:
administering (f) an amino acid composition comprising the following amino acids in the molar ratios specified below: alanine (8.4 to 15.6 moles), arginine (2.4 to 4.6 moles), aspartic acid (not more than one mole), glycine (13.3 to 24.9 moles), histidine (1.8 to 11.9 moles), isoleucine (3.1 to 5.9 moles), leucine (4.3 to 8.1 moles), lysine (6.0 to 11.2 moles) methionine (not more than one mole), phenylalanine (2.6 to 5.0 moles), proline (12.6 to 23.4 moles), serine (1.7 to 3.3 moles) threonine (5.0 to 9.4 moles), tryptophan (1.5 to 2.9 moles), tyrosine (4.2 to 7.8 moles), valine (8.2 to 15.4 moles), and glutamine (0.01 to 20 moles).

11. The method of claim 8 for promoting a process wherein body fats are converted into energy required for physical exercise during and/or after anoxic or anaerobic motions performed under an extremely high load, which comprises:
administering (g) an amino acid composition comprising the following amino acids in the molar ratios specified below: alanine (8.4 to 15.6 moles), arginine (2.4 to 4.6 moles), aspartic acid (not more than one mole), glutamic acid (2.2 to 10.4 moles), glycine (13.3 to 24.9 moles), histidine (1.8 to 11.9 moles), isoleucine (3.1 to 5.9 moles), leucine (4.3 to 8.1 moles), lysine (6.0 to 11.2 moles), methionine (not more than one mole), phenylalanine (2.6 to 5.0 moles), proline (12.6 to 23.4 moles), serine (1.7 to 3.3 moles), threonine (5.0 to 9.4 moles), tyrosine (4.2 to 7.8 moles), valine (8.2 to 15.4 moles), and glutamine (0.01 to 20 moles).

12. The method of claim 8 for promoting a process wherein body fats are converted into energy required for physical exercise during and/or after anoxic or anaerobic motions performed under an extremely high load, which comprises:
administering (h) an amino acid composition comprising the following amino acids in the molar ratios specified below: alanine (8.4 to 15.6 moles), arginine (2.4 to 4.6 moles), glutamic acid (2.2 to 10.4 moles), glycine (13.3 to 24.9 moles), histidine (1.8 to 11.9 moles), isoleucine (3.1 to 5.9 moles), leucine (4.3 to 8.1 moles), lysine (6.0 to 11.2 moles), phenylalanine (2.6 to 5.0 moles), proline (12.6 to 23.4 moles), serine (1.7 to 3.3 moles), threonine (5.0 to 9.4 moles), tryptophan (1.5 to 2.9 moles), tyrosine (4.2 to 7.8 moles), valine (8.2 to 15.4 moles), and glutamine (0.01 to 20 moles).

13. The method of claim 8, wherein an amount of said composition sufficient to reduce fatigue, increase blood sugar level, or decrease lactic acid level, compared to a control subject not receiving said composition, is administered.

14. The method of claim 8, wherein said composition further comprises at least one of trehalose, taurine (Tau), phosphoric acid ethanolamine (P-EtAm), cysteine (Cys), β-alanine, γ-aminobutyric acid (GABA), ornithine (Orn), ethanolamine (EtAm), ammonia ($NH_3$), 1-methyl-histidine (1-MeHis), or 3-methyl-histidine (3-MeHis).

15. The method of claim 1, wherein said composition is administered prior to anoxic or anaerobic exercise.

* * * * *